US009964512B2

(12) United States Patent
Miyai et al.

(10) Patent No.: US 9,964,512 B2
(45) Date of Patent: May 8, 2018

(54) EXHAUST GAS ANALYZING SYSTEM

(71) Applicant: HORIBA, Ltd., Kyoto (JP)

(72) Inventors: Masaru Miyai, Kyoto (JP); Manabu Ito, Kyoto (JP); Masahiro Nishikawa, Kyoto (JP)

(73) Assignee: Horiba, Ltd., Kyoto (JP)

( * ) Notice: Subject to any disclaimer, the term of this patent is extended or adjusted under 35 U.S.C. 154(b) by 213 days.

(21) Appl. No.: 13/900,185

(22) Filed: May 22, 2013

(65) Prior Publication Data

US 2013/0312487 A1 Nov. 28, 2013

(30) Foreign Application Priority Data

May 22, 2012 (JP) ................................ 2012-117044

(51) Int. Cl.
*G01N 27/407* (2006.01)
*F04B 49/00* (2006.01)
*F04B 51/00* (2006.01)

(52) U.S. Cl.
CPC ........... *G01N 27/407* (2013.01); *F04B 49/00* (2013.01); *F04B 51/00* (2013.01); *F04B 2205/09* (2013.01)

(58) Field of Classification Search
CPC ............. G05B 23/027; G05B 23/0283; A61M 1/1086; F04B 49/00; F04B 51/00; F17D 5/06; G01F 1/00; G01F 1/007; G01M 3/02; G01M 3/2807; G01N 1/2252
USPC ....................... 60/277; 73/23.31, 40, 40.5 R, 73/114.69–114.76, 863, 863.01, 863.02, 73/863.03; 417/63; 701/29.1; 715/771, 715/772
See application file for complete search history.

(56) References Cited

U.S. PATENT DOCUMENTS

| | | | |
|---|---|---|---|
| 4,091,674 A | | 5/1978 | Amey |
| 4,432,248 A | | 2/1984 | Lalin |
| 5,477,218 A | | 12/1995 | Manmoto et al. |
| 5,560,199 A | * | 10/1996 | Agustin et al. ................. 60/274 |

(Continued)

FOREIGN PATENT DOCUMENTS

| | | |
|---|---|---|
| CN | 101255952 A | 9/2008 |
| CN | 201653765 U | 11/2010 |

(Continued)

OTHER PUBLICATIONS

Yong Chen, "An Example of Eliminating the Failure of the Air Pump", Printed Technology, Apr. 20, 2000, Issue No. 4, pp. 84.

(Continued)

*Primary Examiner* — Peter Macchiarolo
*Assistant Examiner* — Irving A Campbell
(74) *Attorney, Agent, or Firm* — Brooks Kushman P.C.

(57) ABSTRACT

An exhaust gas analyzing system makes it possible to determine appropriate maintenance timing of sampling pumps in the system, including sampling pumps and provided in a main flow path in order to sample exhaust gas sent from an introduction port, analysis parts provided on the upstream side or downstream side of the sampling pumps and in the main flow path, flow meters provided on the upstream side or downstream side of the analysis parts in the main flow path, and pump abnormality determination parts and for determining abnormality of the sampling pumps by comparing pump flow rates obtained by the flow meters to a predetermined abnormal flow rate.

4 Claims, 2 Drawing Sheets

(56) References Cited

U.S. PATENT DOCUMENTS

| | | | | | |
|---|---|---|---|---|---|
| 8,613,696 | B2 * | 12/2013 | Medvedev | A61M 1/101 600/16 |
| 2010/0229544 | A1 * | 9/2010 | Bollinger | F15B 1/024 60/413 |
| 2013/0103353 | A1 * | 4/2013 | Kloppner | G05B 23/0235 702/182 |

FOREIGN PATENT DOCUMENTS

| | | | | |
|---|---|---|---|---|
| JP | 01-151231 | U | 10/1989 | |
| JP | 07-020015 | | 1/1995 | |
| JP | 07-072050 | | 3/1995 | |
| JP | 07-151680 | | 6/1995 | |
| JP | 11014530 | | 1/1999 | |
| JP | 2000-105178 | | 4/2000 | |
| JP | 2002-270583 | | 9/2002 | |
| JP | 2003-166477 | | 6/2003 | |
| JP | 2004212128 | A | 7/2004 | |
| WO | WO 2010144782 | A1 * | 12/2010 | F04B 15/02 |
| WO | WO 2011013676 | A1 * | 2/2011 | |

OTHER PUBLICATIONS

Office Action dated Oct. 10, 2015 issued for Chinese Patent Application No. 201310178850.6, 10 pgs.

EESR dated Nov. 17, 2017 issued for European Patent Application No. 13 002 667.7.

* cited by examiner

EXHAUST GAS ANALYZING SYSTEM

CROSS-REFERENCE TO RELATED APPLICATION

This application claims priority to JP Application No. 2012-117044, filed on May 22, 2012, the disclosure of which is incorporated in its entirety by reference herein.

TECHNICAL FIELD

The present invention relates to an exhaust gas analyzing system for analyzing exhaust gas discharged from, for example, an internal combustion engine such as a vehicle engine and an external combustion engine such as a steam turbine.

BACKGROUND ART

An exhaust gas analyzing system of this type is as shown in Japanese Patent JPA Hei 11-14530 and includes an introduction port for introducing exhaust gas, an exhaust gas flow path connected to the introduction port, sampling pumps provided on the exhaust gas flow path, and analysis parts provided on the exhaust gas flow path.

Then, the above exhaust gas analyzing system, in which periodic maintenance such as replacement of the sampling pump needs to be performed, is configured in the conventional method to perform maintenance by determination of whether or not maintenance such as replacement is required with the use of cumulative operating time of the sampling pumps or according to predetermined a periodic maintenance period without taking cumulative operating time into consideration.

However, as stated above, when maintenance such as replacement of the sampling pump is performed by using the predetermined cumulative operating time or maintenance period, deterioration of the sampling pumps due to deterioration over time may have been already out of a permissible range even before a lapse of the predetermined cumulative operating time or maintenance period. This means a deteriorated sampling pump is used until the end of the predetermined cumulative operating time or maintenance period, whereby causing sampling performance degradation and therefore resulting in analysis performance degradation in the analyzing system, which is problematic.

Meanwhile, even after a lapse of the predetermined cumulative time or maintenance period, deterioration of the sampling pump may still be within a permissible range. In this case, maintenance such as replacement of usable sampling pump is performed according to a lapse of the predetermined cumulative operating time or maintenance period and a problem arises with necessity of suspending measurement for unnecessary maintenance.

SUMMARY OF INVENTION

Technical Problem

The present invention was achieved to solve the above problems all at once and has an intended object to allow determination of appropriate maintenance timing of sampling pumps in an exhaust gas analyzing system.

Solution to Problem

Specifically, an exhaust gas analyzing system according to the present invention is characterized by including an introduction port for introducing exhaust gas, a main flow path with one end connected to the introduction port, sampling pumps provided in the main flow path in order to sample exhaust gas sent from the introduction part, analysis parts provided on the upstream side or downstream side of the sampling pumps in the main flow path in order to analyze exhaust gas, main flow meters provided on the upstream side or downstream side of the analysis parts in the main flow path in order to confirm whether exhaust gas flows through the analysis parts with a flow rate required for analysis, and pump abnormality determination parts for determining abnormality of the sampling pumps by detecting whether or not pump flow rates of the sampling pumps obtained by using output values of the main flow meters meet predetermined conditions of abnormal functioning.

Here, for the determination of whether or not pump flow rates of the sampling pumps meet predetermined conditions of abnormal functioning, it is considered to determine, for example, whether or not pump flow rates fall in predetermined abnormal flow rates or less or whether or not decrements of pump flow rates per unit time (i.e. inclination in time fluctuation) fall in predetermined abnormal values or less.

In such a system, the pump abnormality determination parts determine abnormality of the sampling pumps by detecting whether or not pump flow rates obtained by using output values of the main flow meters meet predetermined conditions of abnormal functioning, whereby deterioration of the sampling pumps can be objectively determined so as to determine appropriate maintenance timing. Therefore, defects (such as sampling performance degradation and unnecessary maintenance) of pump maintenance caused by using predetermined cumulative time and maintenance period according to the conventional method can be resolved.

In order to enable appropriate exhaust gas measurement by showing a user the tendency of fluctuations of pump flow rates obtained from output values of the main flow meters and predicting time left before pump flow rates meet predetermined conditions of abnormal functioning, the pump abnormality determination parts desirably show secular change of pump flow rates of the sampling pumps in a graph on a display. This will be able to improve usability for a user such that a user can predict time left before reaching abnormal flow rates by looking at secular change of pump flow rates shown in a graph and select measurement which can be made within the remaining time in order to carry out measurement continuously.

It is desirable to further include an upstream-side opening/closing valve and downstream-side opening/closing valves provided on the upstream side and the downstream side of the sampling pumps in the main flow path, exhaust flow paths connected between the sampling pumps and the downstream-side opening/closing valves in the main flow path, exhaust flow meters provided in the exhaust flow paths in order to measure exhaust flow rates in the exhaust flow paths, and a leakage abnormality determination part for checking leakage with the use of the exhaust flow rates while closing the upstream-side opening/closing valve and the downstream-side opening/closing valves and activating the sampling pumps. This does not require a leakage check conducted in the conventional method by causing gas for checking to flow so that gas for checking is no longer needed and running costs can be cut. It is also possible to check leakage in the flow paths disposed between the upstream-side opening/closing valve and the downstream-side opening/closing valves by using the sampling pumps whose maintenance timing is appropriately determined.

The leakage abnormality determination part desirably determines leakage abnormality in the main flow path by calculating leakage rates corresponding to ratio of pump flow rates of the sampling pumps to the exhaust flow rates and comparing the leakage rates to a predetermined abnormal leakage rate. By thus determining abnormal leakage using leakage rates corresponding to ratio of exhaust gas flow rates to pump flow rates (="exhaust flow rate"/"pump flow rate"), it is possible to detect leakage which affects measurement of exhaust gas.

Advantageous Effects of Invention

According to the present invention thus configured, it is possible to determine appropriate maintenance timing for the sampling pumps in the exhaust gas analyzing system and prevent sampling performance degradation and unnecessary maintenance.

DESCRIPTION OF EMBODIMENTS

One embodiment of exhaust gas analyzing system according to the present invention is explained below referring to drawings.

An exhaust gas analyzing system 1 of the present embodiment has an exhaust gas analyzing apparatus, which is provided in a test chamber in which an engine for vehicle or the like not shown is installed, for analyzing exhaust gas emitted from the engine, and a central management apparatus provided in a measurement chamber partitioned from the test chamber. Then, the exhaust gas analyzing apparatus and the central management apparatus send and receive various kinds of data such as analysis data and schedule data to/from each other via, for example, LAN.

Note that a plurality of analyzers that are analysis parts based on, for example different measurement principles is mounted on the exhaust gas analyzing apparatus and each of the analyzers can measure a component such as HC, $NO_x$, CO, and $CO_2$ included in exhaust gas.

Figure 1:
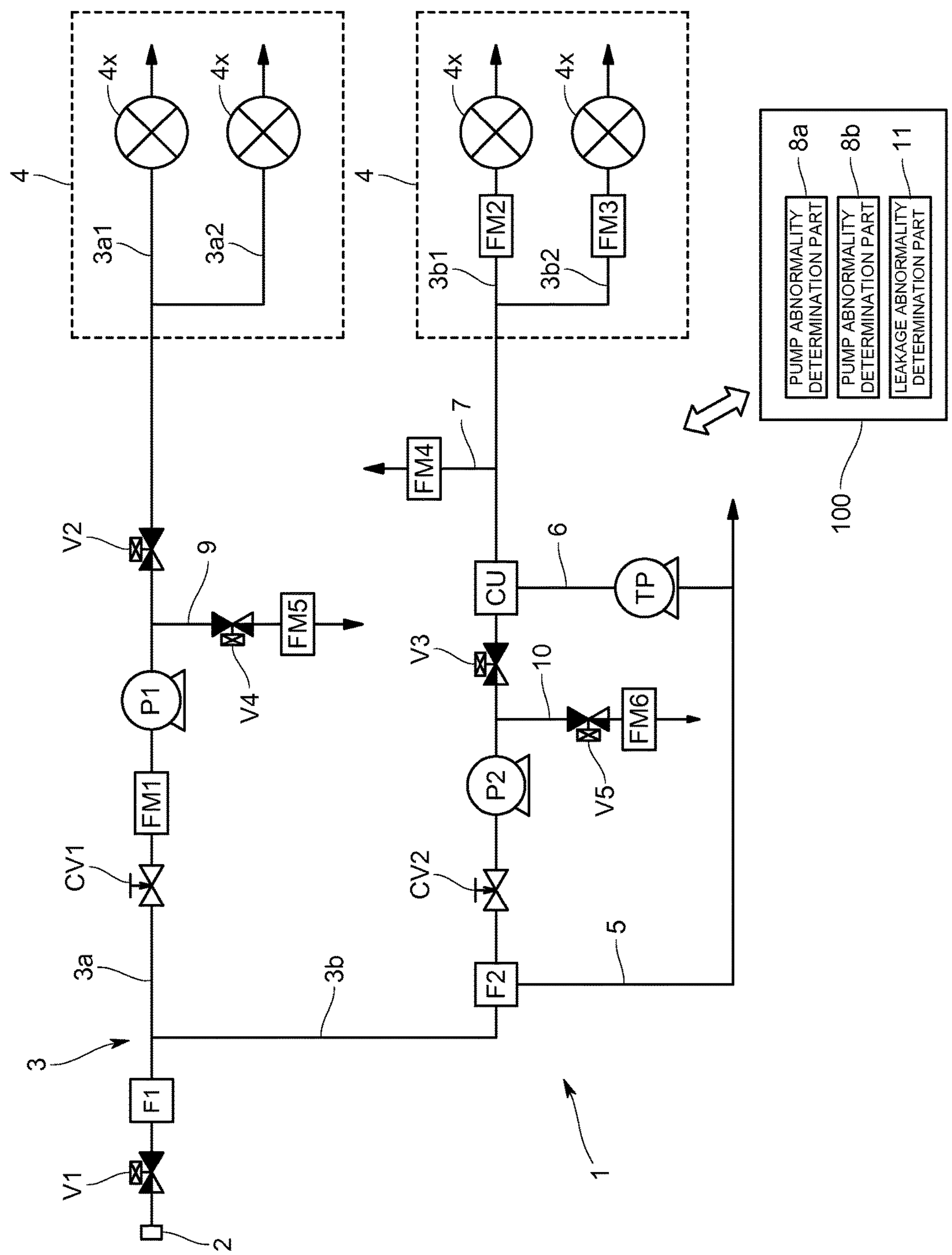
FIG. 1 is a diagram typically showing a structure of an exhaust gas analyzing system according to the present embodiment.

Specifically, the exhaust gas analyzing system 1 is, as shown in FIG. 1, provided with an introduction port 2 for introducing exhaust gas emitted from the engine, and a main flow path 3 with one end connected to the introduction port 2.

The main flow path 3 includes a heated exhaust gas flow path 3*a* in which exhaust gas introduced from the introduction port 2 is heated and the heated exhaust gas is guided to an exhaust gas analyzing apparatus of a heating type, and a normal-temperature exhaust gas flow path 3*b* in which exhaust gas introduced from the introduction port 2 is guided to an exhaust gas analyzing apparatus of a normal temperature type without heating.

Here, the heating-type exhaust gas analyzing apparatus 4 connected to the heated exhaust gas flow path 3*a* includes, for example, THC meter (i.e. hydrogen flame ionization detector or FID), whereas the normal-temperature-type exhaust gas analyzing apparatus 4 connected to the normal-temperature exhaust gas flow path 3*b* includes, for example, CO meter (i.e. non-dispersive infrared analyzer or NDIR), $CO_2$ meter (i.e. non-dispersive infrared analyzer or NDIR), and $NO_x$ meter (i.e. chemiluminescence densitometer or CLD).

The heated exhaust gas flow path 3*a* and the normal-temperature exhaust gas flow path 3*b* are formed by branching off on the downstream side of the introduction port 2. A dust removal filter F1 for removing dust in exhaust gas is provided on the upstream side of the branch point.

One or a plurality of analyzer(s) 4*x* for analyzing predetermined components in heated exhaust gas is provided on the downstream side of the heated exhaust gas flow path 3*a*. Note that FIG. 1 shows the case where two of the analyzers 4*x* are provided, and in the case a plurality of analyzers 4*x* are provided, the heated exhaust gas flow path 3*a* branches off into branch paths 3*a*1 and 3*a*2 each of which is provided with the analyzer 4*x*.

The heated exhaust gas flow path 3*a* is also provided with a sampling pump P1 for sampling exhaust gas sent from the introduction port 2 and introducing to the analyzers 4*x*. The sampling pump P1 allows exhaust gas to flow through the heated exhaust gas flow path 3*a* with a predetermined constant flow rate and is controlled by a controller 100.

On the upstream side of the sampling pump P1, a main flow meter FM1 such as a pressure-type flow meter is provided to measure the flow rate of exhaust gas flown by the sampling pump P1 through the heated exhaust gas flow path 3*a*. There is also a flow rate control valve CV1 provided on the upstream side of the main flow meter FM1 in order to control the flow rate of exhaust gas sampled in the sampling pump P1. In addition, in the middle of the heated exhaust gas flow path 3*a* toward the analyzers 4*x*, a hot hose (not shown) for heating exhaust gas at, for example about 130° C. and other components are installed. There is also a pressure control valve (not shown) provided on the downstream side of the sampling pump P1 in order to control the pressure of exhaust gas flowing into the analyzers 4*x*, and an exhaust flow path for pressure regulation (not shown) is connected to discharge exhaust gas to the outside via the pressure control valve. Owing to the arrangement of the main flow meter FM1 on the upstream side of the sampling pump P1 in the present embodiment, it is unnecessary to provide a flow meter in the exhaust flow path for pressure regulation in order to obtain a pump flow rate.

On the downstream side of the normal-temperature exhaust gas flow path 3*b*, one or a plurality of analyzer(s) 4*x* is provided in order to analyze predetermined components in normal-temperature exhaust gas. Note that FIG. 1 shows the case where two of the analyzers 4*x* are provided, and in the case a plurality of analyzers 4*x* are provided, the normal-temperature exhaust gas flow path 3*b* branches off into branch paths 3*b*1 and 3*b*2 each of which is provided with the analyzer 4*x*.

The normal-temperature exhaust gas flow path 3*b* also includes a sampling pump P2 for sampling exhaust gas sent from the introduction port 2 and introducing to the analyzers 4*x*. The sampling pump P2 allows exhaust gas to flow through the normal-temperature exhaust gas flow path 3*b* with a predetermined constant flow rate and is controlled by the controller 100.

A flow rate control valve CV2 is provided on the upstream side of the sampling pump P2 in order to control the flow rate of exhaust gas sampled in the sampling pump P2. A filter F2 is further provided on the upstream side of the flow rate control valve CV2 in order to remove components such as moisture included in exhaust gas. Water removed by the filter F2 is drained to the outside via a drain path 5. A cooling unit CU for cooling exhaust gas is also provided on the downstream side of the sampling pump P2 and dew condensation water generated in the cooling unit CU is also drained to the outside via a drain path 6. Note that the drain path 6 is provided with a drain pump TP such as a tubing pump.

The normal-temperature gas flow rate 3*b* includes main flow meters FM2 and FM3 such as thermal flow meters provided on the upstream side of the analyzers 4*x* in the branch paths 3*b*1 and 3*b*2, each of which has the analyzer 4*x*, in order to measure exhaust gas flowing through the analyzers 4*x*, respectively. These main flow meters FM2 and FM3 are arranged in the inside of the normal-temperature-type exhaust gas analyzing apparatus 4. Here, the arrangement in the inside of the exhaust gas analyzing apparatus 4 includes two states one of which is to accommodate or hold various analyzers 4*x* within a single frame in the exhaust gas analyzing apparatus 4 and the other one is to hold the analyzers 4*x* by means of rack or the like. The normal-temperature exhaust gas flow path 3*b* is also provided with a pressure control valve (not shown) on the upstream side of the main flow meters FM2 and FM3 in order to control the pressure of exhaust gas flowing into the analyzers 4*x*, and an exhaust flow path 7 for pressure regulation is connected for the pressure control valve to discharge exhaust gas to the outside. The pressure control valve also prevents exhaust gas from flowing through the analyzers 4*x* more than necessary. The exhaust flow path 7 for pressure regulation is also provided with an exhaust flow meter FM4 such as a thermal flow meter for measuring an exhaust flow rate Thus, the exhaust gas analyzing system 1 of the present embodiment has a maintenance check function for checking maintenance of the sampling pumps P1 and P2 provided in the heated exhaust gas flow path 3*a* and the normal-temperature exhaust gas flow path 3*b* of the main flow path 3 respectively, and a leakage check function for checking leakage in the heated exhaust gas flow path 3*a* and the normal-temperature exhaust gas flow path 3*b*.

Firstly, the maintenance check function is explained. The maintenance check function for the sampling pump P1 provided in the heated exhaust gas flow path 3*a* is composed of the main flow meter FM1 provided on the upstream side of the sampling pump P1 and a pump abnormality determination part 8*a* which determines abnormality of the sampling pump P1 by detecting whether or not a pump flow rate of the sampling pump P1 obtained from an output value of the main flow meter FM1 meets a predetermined condition of abnormal functioning.

The pump abnormality determination part 8*a* is composed of the controller 100 which is made of a general-purpose or exclusive computer having CPU, internal memory, input/output interface, AD converter, display and other components.

Specifically, the pump abnormality determination part 8*a* calculates a pump flow rate in the sampling pump P1 with the use of an exhaust gas flow rate obtained by the main flow meter FM1. The heated exhaust gas flow path 3*a* is configured such that the main flow meter FM1 is provided on the upstream side of the sampling pump P1 in one heated exhaust gas flow path 3*a*, whereby an exhaust gas flow rate which is a value measured in the main flow meter FM1 corresponds to a pump flow rate of the sampling pump P1. Then, the pump abnormality determination part 8*a* determines whether the sampling pump P1 is abnormal by comparing a pump flow rate of the sampling pump P1 to a predetermined abnormal flow rate. Here, when a pump flow rate falls in a predetermined abnormal flow rate or less, the pump flow rate meets a predetermined condition of abnormal functioning.

The predetermined abnormal flow rate in the present embodiment is set in two stages. That is, there are two kinds of predetermined abnormal flow rates including a first abnormal flow rate Qx1 corresponding to a predetermined flow rate reduced from an initial flow rate of exhaust gas flown by the sampling pump P1 through the heated exhaust gas flow path 3*a*, and a second abnormal flow rate Qx2 corresponding to a predetermined flow rate reduced from the first abnormal flow rate Qx1. The first abnormal flow rate Qx1 indicates it is not the maintenance timing of the sampling pump P1 yet but the maintenance period comes close shortly. Meanwhile, the second abnormal flow rate Qx2 indicates the sampling pump P1 falls in the maintenance timing with a minimum flow rate required for the analyzers 4*x*.

Then, the pump abnormality determination part 8*a* notifies a user of precaution when an exhaust gas flow rate obtained by the main flow meter FM1 is less than the first abnormal flow rate Qx1. Therefore, the user can find out the maintenance timing of the sampling pump P1 is not far away. The pump abnormality determination part 8*a* also gives the user an alarm when an exhaust gas flow rate obtained by the main flow meter FM1 is less than the second abnormal flow rate Qx2. Therefore, a user can find out the sampling pump P1 falls in the maintenance timing.

Figure 2:
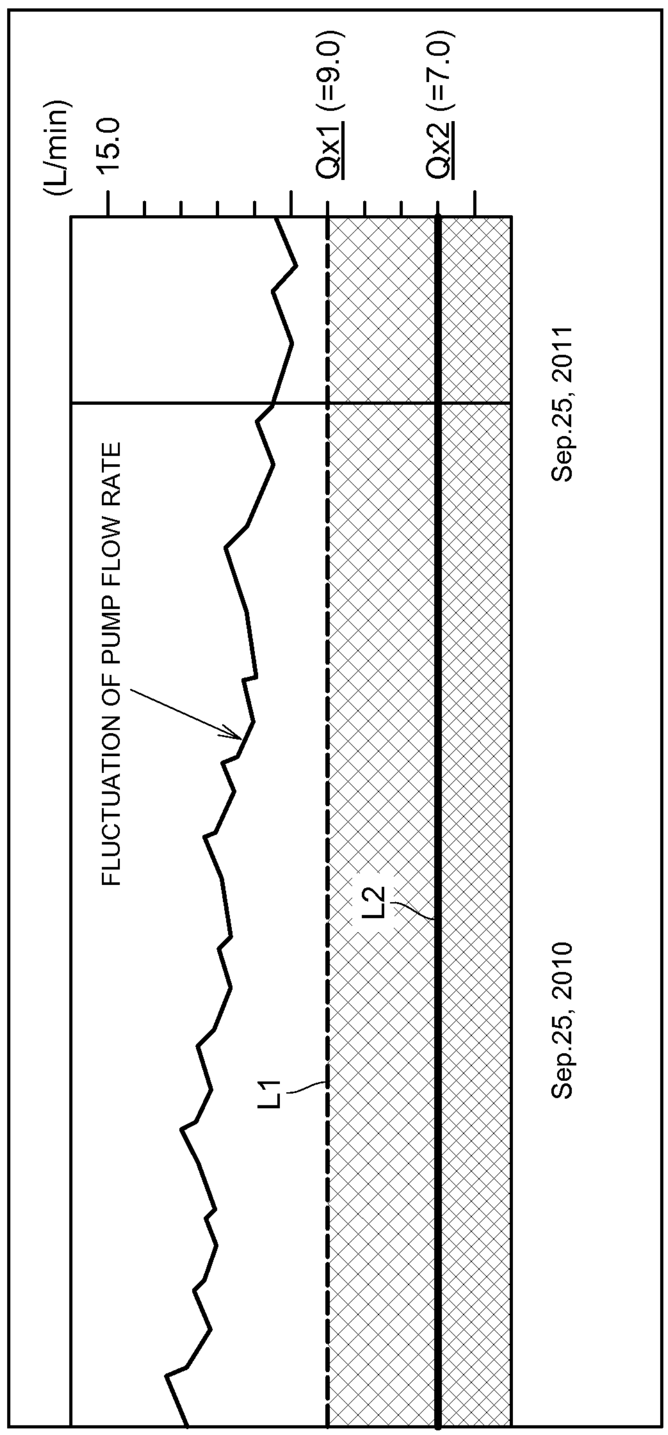
FIG. 2 is a diagram showing a graph display on a display in the same embodiment.

The pump abnormality determination part 8*a* also shows a pump flow rate of the sampling pump P1 in a graph on the display as shown in FIG. 2. At this time, a precaution line L1 corresponding to the first abnormal flow rate Qx1 and an alarm line L2 corresponding to the second abnormal flow rate Qx2 are shown on the graph. By thus showing the trend of fluctuations of a pump flow rate in the sampling pump P1 to a user in a graph, it is made possible to predict time left before a pump flow rate reaches the abnormal flow rates (Qx1 and Qx2) and appropriately perform measurement of exhaust gas.

A maintenance check function for the sampling pump P2 provided in the normal-temperature exhaust gas flow path 3*b* is composed of the plural main flow meters FM2 and FM3 provided in the branch paths 3*b*1 and 3*b*2 respectively on the downstream side of the sampling pump P2, the exhaust flow meter FM4 provided in the exhaust flow path 7 for pressure regulation, and a pump abnormality determination part 8*b* for determining whether the sampling pump P2 is abnormal by detecting whether or not a pump flow rate of the sampling pump P2 obtained from output values of the plural main flow meters FM2 and FM3 and the exhaust flow meter FM4 meets a predetermined condition of abnormal functioning.

The pump abnormality determination part 8*b* is composed of the controller 100 in the same manner as the pump abnormality determination part 8*a* of the heated exhaust gas flow path 3*a*.

Specifically, the pump abnormality determination part 8*b* calculates a pump flow rate in the sampling pump P2 from exhaust gas flow rates obtained by the plural main flow meters FM2 and FM3 and an exhaust flow rate obtained by the exhaust flow meter FM4. More precisely, the pump abnormality determination part 8*b* calculates a total value by adding exhaust gas flow rates obtained by the plural main flow meters FM2 and FM3 and an exhaust flow rate obtained by the exhaust flow meter FM4 and uses the total value as the pump flow rate. Then, the pump abnormality determination part 8*b* determines whether the sampling pump P2 is abnormal by comparing the pump flow rate to a predetermined abnormal flow rate. Here, when the pump flow rate falls in the predetermined abnormal flow rate or less, the pump flow rate meets a predetermined condition of abnormal functioning. Note that the abnormality determination method in the pump abnormality determination part 8*b* is the same as the pump abnormality determination part 8*a*.

Next, the leakage check function is explained. In the leakage check function of the present embodiment, a leakage check is conducted for both the heated exhaust gas flow path 3*a* and the normal-temperature exhaust gas flow path 3*b* simultaneously. Specifically, the leakage check function is composed of an upstream-side opening/closing valve V1 and downstream-side opening/closing valves V2 and V3 provided on the upstream side and the downstream side of the sampling pumps P1 and P2 respectively in the main flow path 3, exhaust flow paths 9 and 10 connected between the sampling pump P1 and the downstream-side opening/closing valve V2 and between the sampling pump P2 and the downstream-side opening/closing valve V3 respectively in the main flow path 3, exhaust flow meters FM5 and FM6 provided in the exhaust flow paths 9 and 10 in order to measure flow rates in the exhaust flow paths 9 and 10 respectively, and a leakage abnormality determination part 11 for checking leakage with the use of exhaust flow rates obtained by the exhaust flow meters FM5 and FM6 while closing the upstream-side opening/closing valve V1 and the downstream-side opening/closing valves V2 and V3 and activating the sampling pumps P1 and P2.

The upstream-side opening/closing valve V1, which should be desirably arranged close to the downstream side of the introduction port 2, is provided between the introduction port 2 and the dust removal filter F1 on the upstream side of the branch point of the exhaust gas flow paths 3*a* and 3*b* in the present embodiment. Note that the upstream-side opening/closing valve V1 may also be provided in each of the exhaust gas flow paths 3*a* and 3*b* on the upstream side thereof. It should also be noted that the upstream-side opening/closing valve V1 is a solenoid valve controlled by the controller 100.

The downstream-side opening/closing valve V2 of the heated exhaust gas flow path 3*a* is also provided between the sampling pump P1 and the branch point of the branch paths 3*a*1 and 3*a*2 in the heated exhaust gas flow path 3*a*. Meanwhile, the downstream-side opening/closing valve V3 of the normal-temperature exhaust gas flow path 3*b* is provided between the sampling pump P2 and the cooling unit CU in the normal-temperature exhaust gas flow path 3*b*. Note that the downstream-side opening/closing valves V2 and V3 are solenoid valves controlled by the controller 100.

Then, the exhaust flow path 9 of the heated exhaust gas flow path 3*a* is connected between the sampling pump P1 and the downstream-side opening/closing valve V2 in the heated exhaust gas flow path 3*a*. The exhaust flow path 9 is provided with an opening/closing valve V4 and the exhaust flow meter FM5 in this order. Meanwhile, the exhaust flow path 10 of the normal-temperature exhaust gas flow path 3*b* is connected between the sampling pump P2 and the downstream-side opening/closing valve V3 in the normal-temperature exhaust gas flow path 3*b*. The exhaust flow path 10 is provided with an opening/closing valve V5 and the exhaust flow meter FM6 in this order. Note that the opening/closing valves V4 and V5 are solenoid valves controlled by the controller 100.

The leakage abnormality determination part 11 is composed of the controller 100 made of general-purpose or exclusive computer having CPU, internal memory, input/output interface, AD converter, display and other components. Note that the leakage abnormality determination part 11 may also be composed of a controller which is physically separated from the controller 100 to constitute the pump abnormality determination parts 8*a* and 8*b*.

Specifically, the leakage abnormality determination part 11 causes, in a leakage check process, the upstream-side opening/closing valve V1 and the downstream-side opening/closing valves V2 and V3 to close, and the opening/closing valves V4 and V5 provided in the exhaust flow paths 9 and 10 respectively to open. Then, the sampling pumps P1 and P2 are activated to discharge gas from flow paths disposed between the upstream-side opening/closing valve V1 and the sampling pumps P1 and P2. Then, output values sent from the exhaust gas flow meters FM5 and FM6 at this time are obtained. Note that an output value of the exhaust flow meter FM5 is zero when there is no leakage between the upstream-side opening/closing valve V1 and the sampling pump P1 in the heated exhaust gas flow path 3*a*. An output value of the exhaust flow meter FM6 is also zero when there is no leakage between the upstream-side opening/closing valve V1 and the sampling pump P2 in the normal-temperature exhaust gas flow path 3*b*. The present embodiment is configured to perform a leakage check on the upstream side of the sampling pumps P1 and P2 by the leakage check function in measurement of exhaust gas because impact of leakage is more significant on the upstream side of the sampling pumps P1 and P2 that are accompanied by a negative pressure.

The leakage abnormality determination part 11 also obtains, before the leakage check process, an exhaust gas flow rate (i.e. pump flow rate on the heated side) in measurement obtained by the main flow meter FM1 in the heated exhaust gas flow path 3*a*, and a total value (i.e. pump flow rate on the normal temperature side) calculated by adding exhaust gas flow rates in measurement obtained by the plural main flow meters FM2 and FM3 and an exhaust flow rate in measurement obtained by the exhaust flow meter FM4 in the normal-temperature exhaust gas flow path 3*b*.

Then, the leakage abnormality determination part 11 calculates, in the heated exhaust gas flow path 3*a*, a leakage rate which is a ratio of a pump flow rate on the heated side to an exhaust flow rate (or leakage flow rate) obtained by the exhaust flow meter FM5, and determines leakage abnormality in the heated exhaust gas flow path 3*a* by comparing the leakage rate to a predetermined abnormal leakage rate (e.g. 0.5%). The leakage abnormality determination part 11 also calculates, in the normal-temperature exhaust gas flow path 3*b*, a leakage rate which is a ratio of a pump flow rate on the normal-temperature side to an exhaust flow rate (or leakage flow rate) obtained by the exhaust flow meter FM6, and determines leakage abnormality in the normal-temperature exhaust gas flow path 3*b* by comparing the leakage rate to a predetermined abnormal leakage rate (e.g. 0.5%).

When the leakage abnormality determination part 11 thus determines leakage abnormality in the heated exhaust gas flow path 3*a* or the normal-temperature exhaust gas flow path 3*b*, a display to notify a user of leakage abnormality is shown on the display.

In the exhaust gas analyzing system 1 which is thus configured according to the present embodiment, the pump abnormality determination parts 8*a* and 8*b* determine abnormality of the sampling pumps P1 and P2 by calculating pump flow rates in the sampling pumps P1 and P2 with the use of exhaust gas flow rates obtained by the main flow meters FM1, FM2, and FM3 and comparing the pump flow rates to predetermined abnormal flow rates, whereby making it possible to determine deterioration of the sampling pumps P1 and P2 objectively so as to determine appropriate maintenance timing. It is therefore possible to resolve defects (such as sampling performance degradation and unnecessary maintenance) of pump maintenance caused by using predetermined cumulative operation time and maintenance period according to the conventional method. Also, because pump flow rates are calculated by using output values of the main flow meters FM1, FM2 and FM3 for measuring the flow rate of exhaust gas flowing through the analyzers 4*x*, it is unnecessary to separately arrange a measurement instrument for measuring pump flow rates of the sampling pumps P1 and P2 so that appropriate maintenance timing can be determined without making the system structure complicated.

In addition, owing to the leakage abnormality determination part 11 which determines abnormal leakage by using leakage rates corresponding to the ratio of pump flow rates to leakage flow rates (="leakage flow rate"/"pump flow rate on the heated side" and "leakage flow rate"/"pump flow rate on the normal temperature side"), leakage which affects measurement of exhaust gas can be preferably detected.

Note that the present invention is not limited to the above embodiment. For example, as opposed to the configuration in the above embodiment in which one main flow meter is provided on the upstream side of the sampling pump in the heated exhaust gas flow path 3*a*, the main flow meter may be provided on the downstream side of the sampling pump or a plurality of main flow meters may also be provided in a plurality of branch paths to which a plurality of analyzers is connected one by one.

Although the main flow path branches off into two paths including the heated exhaust gas flow path and the normal-temperature gas flow path in the above embodiment, the main flow path may also be provided as a heated exhaust gas flow path or a normal-temperature exhaust gas flow path without branching off, or may also branch off into more than two heated exhaust gas flow paths or more than two normal-temperature exhaust gas flow paths.

Instead of showing pump flow rates of the sampling pumps in a graph on the display, it may be configured, without displaying a graph, to notify a user of precaution when pump flow rates fall in the first abnormal flow rate or less and give a user an alarm when pump flow rates fall in the second abnormal flow rate or less.

The leakage function is not limited to calculate leakage rates to compare to predetermined abnormal leakage rates, and may compare exhaust flow rates (leakage flow rates) obtained from the exhaust flow meters to predetermined leakage flow rates (thresholds).

Furthermore, the leakage check may be carried out by providing pressure sensors between the upstream-side opening/closing valve and the sampling pumps and using pressure values that are obtained by activating the sampling pumps while closing the upstream-side opening/closing valve.

In addition, although the leakage check is carried out for both the heated exhaust gas flow path and the normal-temperature exhaust gas flow path simultaneously in the present embodiment, it may be carried out for each of the exhaust gas flow paths. Leakage check for both the heated exhaust gas flow path and the normal-temperature exhaust gas flow path may also be carried out by closing the upstream-side opening/closing valve V1 and the downstream-side opening/closing valves V2 and V3 and activating only the sampling pump provided in one of the exhaust gas flow paths. For a leakage rate obtained at this time, for example, a ratio (="leakage flow rate"/"pump flow rate on the heated side"+"pump flow rate on the normal temperature side") of a leakage flow rate to a pump flow rate on the heated side and a pump flow rate on the normal temperature side is considered.

The controller may also be provided with a necessary flow rate determination part in which whether or not exhaust gas flows through the analyzers with a flow rate required for measurement is determined by obtaining output values sent from the main flow meters.

The exhaust gas analyzing system may be provided with an introduction port for introducing exhaust gas, a main flow path with one end connected to the introduction port, sampling pumps provided in the main flow path in order to sample exhaust gas sent from the introduction port, analysis parts provided on the upstream side or downstream side of the sampling pumps in the main flow path in order to analyze exhaust gas, an upstream-side opening/closing valve and downstream-side opening/closing valves provided on the upstream side and the downstream side of the sampling pumps in the main flow path, exhaust flow paths connected between the sampling pumps and the downstream-side opening/closing valves in the main flow path, exhaust flow meters provided in the exhaust flow paths in order to measure exhaust flow rates in the exhaust flow paths, and a leakage abnormality determination part for checking leakage with the use of the exhaust flow rates while closing the upstream-side opening/closing valve and the downstream-side opening/closing valves and activating the sampling pumps. With this system, running costs can be cut because the conventional leakage check conducted by causing gas for checking to flow is unnecessary and therefore gas for checking is no longer needed. It is also possible to conduct a leakage check in flow paths disposed between the upstream-side opening/closing valve and the downstream-side opening/closing valves by using the sampling pumps whose maintenance timing is appropriately determined.

Although the above embodiment is provided for analyzing exhaust gas in the engine, it may also be used for analyzing exhaust gas emitted from an external combustion engine such as steam turbine.

In addition the above, the present invention is not limited to the above embodiment and can also be modified variously in a range without deviating from the gist of the present invention.

DESCRIPTION OF REFERENCE NUMERALS

1 Exhaust gas analyzing system
2 Introduction port
3 Main flow path
4*x* Analyzer (Analysis part)
P1, P2 Sampling pump
FM1, FM2, FM3 Main flow meter
V1 Upstream-side opening/closing valve
V2, V3 Downstream-side opening/closing valve
8*a*, 8*b* Pump abnormality determination part
9, 10 Exhaust flow path
FM5, FM6 Exhaust flow meter
11 Leakage abnormality determination part

What is claimed is:

1. An exhaust gas analyzing system comprising:

an introduction port for introducing exhaust gas;

a main flow path with one end connected to the introduction port;

a sampling pump provided in the main flow path to sample exhaust gas sent from the introduction port;

an upstream-side opening/closing valve provided on an upstream side of the sampling pump in the main flow path;

a downstream-side opening/closing valve provided on a downstream side of the sampling pump in the main flow path;

an exhaust flow path connected between the sampling pump and the downstream-side opening/closing valve in the main flow path;

an exhaust flow meter provided in the exhaust flow path to measure an exhaust flow rate in the exhaust flow path;

an analysis part provided on the upstream side or downstream side of the sampling pump in the main flow path to analyze exhaust gas;

a main flow meter provided on an upstream side or downstream side of the analysis part in the main flow path to confirm whether exhaust gas flows through the analysis part with a flow rate required for analysis; and a controller for checking leakage with use of the exhaust flow rate while closing the upstream-side opening/closing valve and the downstream-side opening/closing valve and activating the sampling pump, and for determining abnormality of the sampling pump by detecting whether or not a pump flow rate of the sampling pump obtained by using output values of the main flow meter meets predetermined conditions of abnormal functioning, and for showing in a graph, having a pump flow rate axis and a date axis, on a display a change over time of the pump flow rate of the sampling pump, month or day or both, a precaution line corresponding to a first abnormal flow rate that is a predetermined flow rate, and an alarm line corresponding to a second abnormal flow rate that is a predetermined flow rate reduced from the first abnormal flow rate, wherein the precaution line indicates that a maintenance time is near due to deterioration of the sampling pump, and wherein the alarm line indicates that the sampling pump has reached the maintenance time due to the deterioration of the sampling pump.

2. The exhaust gas analyzing system according to claim 1, wherein the controller determines leakage abnormality in the main flow path by calculating a leakage rate corresponding to a ratio of the pump flow rate of the sampling pump to the exhaust flow rate and comparing the leakage rate to a predetermined abnormal leakage rate.

3. An exhaust gas analyzing system comprising:

an introduction port for introducing exhaust gas;

a main flow path with one end connected to the introduction port;

a sampling pump provided in the main flow path to sample exhaust gas sent from the introduction port;

an analysis part provided on an upstream side or downstream side of the sampling pump in the main flow path to analyze exhaust gas;

a main flow meter provided on an upstream side or downstream side of the analysis part in the main flow path to confirm whether exhaust gas flows through the analysis part with a flow rate required for analysis;

a controller for determining abnormality of the sampling pump by detecting whether or not a pump flow rate of the sampling pump obtained by using output values of the main flow meter meets predetermined conditions of abnormal functioning;

an upstream-side opening/closing valve provided on the upstream side of the sampling pump in the main flow path;

a downstream-side opening/closing valve provided on the downstream side of the sampling pump in the main flow path;

an exhaust flow path connected between the sampling pump and the downstream-side opening/closing valve in the main flow path;

an exhaust flow meter provided in the exhaust flow path to measure an exhaust flow rate in the exhaust flow path; and a leakage abnormality determination part for checking leakage with the use of the exhaust flow rate while closing the upstream-side opening/closing valve and the downstream-side opening/closing valve and activating the sampling pump.

4. A method for operating an exhaust gas analyzing system including an introduction port, a main flow path with one end connected to the introduction port, a sampling pump provided in the main flow path, an analysis part provided on an upstream side or downstream side of the sampling pump in the main flow path, a main flow meter provided on an upstream side or downstream side of the analysis part in the main flow path, a controller, an upstream-side opening/closing valve provided on the upstream side of the sampling pump in the main flow path, a downstream-side opening/closing valve provided on the downstream side of the sampling pump in the main flow path, an exhaust flow path connected between the sampling pump and the downstream-side opening/closing valve in the main flow path, an exhaust flow meter provided in the exhaust flow path, and a leakage abnormality determination part, the method comprising:

introducing, via the introduction port, exhaust gas;

sampling, via the sampling pump, exhaust gas sent from the introduction port;

analyzing, via the analysis part, exhaust gas;

confirming, via the main flow meter, whether exhaust gas flows through the analysis part with a flow rate required for analysis;

determining, via the controller, abnormality of the sampling pump by detecting whether or not a pump flow rate of the sampling pump obtained by using output values of the main flow meter meets predetermined conditions of abnormal functioning;

measuring, via the exhaust flow meter, an exhaust flow rate in the exhaust flow path; and checking, via the leakage abnormality determination part, leakage with the use of the exhaust flow rate while closing the upstream-side opening/closing valve and the downstream-side opening/closing valve and activating the sampling pump.

* * * * *